United States Patent [19]

de Andrade Brüning

[11] Patent Number: 4,889,813

[45] Date of Patent: Dec. 26, 1989

[54] PROCESS FOR DETERMINING THE POLARITY OF A CRUDE OIL

[75] Inventor: Inái M. R. de Andrade Brüning, Rio de Janeiro, Brazil

[73] Assignee: Petroleo Brasileiro S.A. - Petrobras, Rio de Janeiro, Brazil

[21] Appl. No.: 222,662

[22] Filed: Jul. 21, 1988

[30] Foreign Application Priority Data

Jul. 21, 1987 [BR] Brazil ............................. PI-8703790

[51] Int. Cl.$^4$ ............................................. G01N 30/02
[52] U.S. Cl. ....................................... 436/60; 422/89; 422/104; 436/140
[58] Field of Search ................... 422/89, 104; 436/140

[56] References Cited

PUBLICATIONS

Ettre, L. S. "The Kováts Retention Index System", Anal. Chem. 36(8):31A–41A, 1964.
McReynolds, W. O., "Characterization of Some Liquid Phases", J. of Chromatog. Sci., 8:685–691, 1970.
Rohrschneider, L., "Die Vorausberechnung von gaschromatographischen retentionzeiten aus statistisch ermittelten 'polaritäten'", J. Chromatog., 17:1–12, 1965.
Rohrschneider, L., "Eine methode zur charakterisierung von gaschromatographischen trennflüssigkeiten", J. of Chromatog., 22:6–22, 1966.
Rummens, F. H. A., "Intermolecular interactions in nuclear magnetic resonance. X. A site-specific continuum model for the gas-to-liquid shifts of nonpolar solutes".
Applications to proton medium shifts and the determination of cavity radii, Can. J. Chem., 54:254–269, 1976.
McNair, H. M. and Bonelli, E. J., "Basic Gas Chromatography", pp. 72–79; 123–135, 1969.
Kosower, E. M. "Spectroscopie Ultraviolette et Mesure Empirique de la Polaritédu Solvant (Constant Z)", J. Chem. Phys., 61:230–235, 1964.
Kováts, E. "206, Gas-chromatographische charakterisierung organischer verbindungen. Teil 1:Retentionsindices aliphatischer Halogenide, Alkohole, Aldehyde and Ketone", Helv. Chim. Acta, 41:1915–1932, 1958.

Primary Examiner—Barry S. Richman
Assistant Examiner—Marcella Iris Fruchter
Attorney, Agent, or Firm—Sughrue, Mion, Zinn, Macpeak & Seas

[57] ABSTRACT

A process for determining the polarity of a crude oil or heavy fraction thereof in which the retention times are measured when a series of substances is contacted with a chromatographic column of crude oil, the retention times are measured when these substances are contacted with a chromatographic column of a second substance usually non-polar and the relative polarity of the oil determined from the times measured.

7 Claims, No Drawings

PROCESS FOR DETERMINING THE POLARITY OF A CRUDE OIL

This invention relates to a process for determining the polarity of a crude oil or a heavy fraction thereof, using the oil as a stationary phase, putting one or more known substances in contact with the crude oil and measuring the interactions between the crude oil and the known substances, using inverted gaseous phase chromatography.

It is well known to use gas phase chromatography or gas liquid chromatography or gas chromatography to analyze substances by contacting them with a liquid or with a liquid on a support. The liquid is the stationary phase and the analyte is the mobile phase.

In inverted chromatography, however, the stationary phase is the analyte and the mobile phase is a known substance or, more usually, a series of known substances, whose interactions with the stationary phase are measured. Adsorption and desorption of the mobile phase may occur between the phases in gas chromatography, due to the action of the inert gas which drags the vaporized substances contained in the mobile phase through a solid bed which contains the stationary phase.

Interactions such as adsorption relate to the polarities of the substances between which they occur. The polarity of a substance is the ability of its molecule to have, at two distinct points, different or opposing characteristics, arising from the heterogeneous distribution of electronic charge along its molecular structure. The polarity of a given substance is the result of the polarity of atomic links. Links between equivalent atoms or groups of the same electronic density are non-polar; links between different atoms, or groups with different electronegativities result in polar links. A polar molecule has an electrical moment, a dielectric constant and a dipole moment.

When the molecular polarity of a given organic substance is evaluated, both its permanent or isolated polar characteristic (the intrinsic polarity of the molecule) and its polarity resulting from external polarization of the molecule (the influence of its environment) must be considered. This latter polarity results from the forces of interaction between the molecule and its surroundings.

Paraffinic hydrocarbons or alkanes are non-polar, the dipole moment of methane being equal to zero. Aromatic hydrocarbons, however, although their links are between equivalent atoms, have localized electronic densities and are polarizable. Thus in a polar solvent medium, they have a significant induced polarity. If a given organic molecule has one or more heteroatoms, its polarity increases strongly, as does its electrostatic effect and molecular interactions.

Crude oils consist of an extremely complex mixture of substances whose chemical nature depends on their origin and geologic history. Composition and polarity are intimately associated. The chemical composition, particularly, determines the polarity of a crude oil and its fractions. The polarity of a crude oil represents the synergic action of the polarities of its components.

One of the problems of crude oil analysis is to determine the polarity of the oil. This is important since the polarity determines the behaviour of crude oils in industrial operations such as production, treatment, transportation and refining.

Saturated and aromatic hydrocarbons always predominate in the composition of crude oils. In lower proportions, there are other components whose molecules contain heteroatoms such as nitrogen, oxygen, sulphur and metals. These compounds show polar characteristics and, even when present in small amounts, are responsible for difficulties in the production, transfer and industrial use of crude oils. There is, therefore, a strong interest in evaluating these compounds, but their large variety and small concentrations make their analysis extremely difficult.

It is known that these heteroatomic compounds are concentrated in the heaviest fractions of crude oils, which are consequently the most polar. Such heteroatomic compounds are traditionally referred to as resins and asphaltenes and include a wide variety of chemical groups such as naphthenic acids, carboxylic acids, quinolines, carbazoles, phenols, pyridines, thiophenols, benzothiophenes, alkylphenols, thiols, thiophenes, etc. All of these are polar or polarizable molecules and the polarity, resulting from their mixture and synergistic action, both among themselves and with the predominantly non-polar medium of petroleum hydrocarbons and fractions, results in the polarity shown by crude oil and its fractions.

Other properties in addition to adsorption relate to polarity. No physical property in isolation however, is capable of evaluating fully and correctly the polarity, not even of a pure substance. For a crude oil, the difficulty is evidently much greater. Physical properties such as dielectric constant, dipole moment, refractive index, vaporization heat, boiling point, etc., are all known to be related to the polarity of the substance.

Attempts have been made to establish empiric polarity parameters, based on spectroscopic methods, such as in the papers by KOSOWER, E. M. (J. Chem. Phys., 61:230, 1964) and RUMMENS, F. H. A. (Can. J. Chem., 54:254, 1976) or on chromatographic methods, such as in the papers by ROHRSCHNEIDER, L. (J. Chromatog., 17:1-12, 1965 and ibidem, 22:6-22, 1966), Mc REYNOLDS, W. O. (J. of Chromatog. Sci. 8:685, 1970), KOVATS, E. (Helv. Chim. Acta, 41:1915, 1958), ETTRE, L. S. (Anal. Chem., 36(8): 31A-41A, 1964) and MC NAIR, H. M. & BONELLI E. J. (*Basic Gas Chromatography*, Palo Alto—Calif., Varian, 1968). Such papers referred to pure substances. The applicants are not aware of any report on the mean of measuring the polarity of crude oils. Measuring, by means of nuclear magnetic resonance, the polarity of a mixture of three components which simulates a crude petroleum, was disclosed in French patent application FR No. 2,495,780, published on June 11, 1982, by M. AMAT.

The present invention aims to provide a means of measuring the polarity of complex mixtures of insufficiently known polar compounds.

The present invention uses chromatographic techniques such as those known in the references in a novel process to obtain the relative chemical polarity of each petroleum or petroleum product tested.

The present invention provides a process for determining the relative polarity of a crude oil or fraction thereof comprising:

(a) contacting a known test substance with a stationary phase of the crude oil or fraction in a gas chromatography column, and measuring the interaction between the test substance and the oil;

(b) contacting the known test substance used in (a) with a stationary phase of a second substance in a gas chromatography column and measuring the interaction between the test substance and the second substance;

(c) determining the polarity of the crude oil relative to the second substance from the measurements obtained in (a) and (b).

In particular the chemical polarity of a crude oil or its heavy fractions may be determined by means of a process which includes:

(a) Preparing a gas chromatography column in which the crude oil or its heavy fraction is used as the stationary phase.

(b) Measuring how such a stationary phase interacts with certain known substances, when the latter are injected into the column thus prepared. For each substance a first value is obtained.

(c) Preparing a second gas chromatography column, now with a strongly non-polar substance as the stationary phase and considered to be of zero polarity.

(d) Measuring how such a non-polar stationary phase interacts with the same substances previously injected, but now injected into the non-polar phase column. For each substance a second value is obtained.

(e) From the first and second values a third one is calculated one for each known substance.

(f) From the values calculated in e for all the known substances, the polarity is calculated.

The following description is of a general procedure which utilizes the concepts of the present invention.

Crude oils or their heavy fractions are used as dispersed stationary phases over an inert support of siliceous material containing variable amounts of aluminium and iron oxide, so as to completely and homogeneously cover the support. Since crude oils have light components which would prevent the oils being used in gas chromatography, their heavy cut in the range of 200° C. or 260° C. is used, i.e. lighter components with boiling points below 200° C. or 260° C. are removed. The stationary phase is prepared using the crude oil which has previously been deprived of its components with boiling point below e.g. 200° C. Components with boiling point below 200° C. or 260° C. do not in practice contribute to the polarity and their elimination does not affect it, particularly if the relative polarity of the crude oil is to be determined.

To cover the support with the stationary phase substance, a well known chromatographic technique may be applied. The crude oil, already deprived of its components of low boiling point, is dissolved in a solvent and mixed with said inert support; the solvent is removed by evaporation, stirring constantly. What remains is petroleum cut (crude oil deprived of its light components) deposited over the inert support, and this will fill the chromatographic processing column.

The coated support is then used to fill the metallic tube, as usual in the preparation of a gas chromatographic column. The column is arranged in a chromatographic apparatus containing all devices usually required for the operation of chromatographic analysis—injector, detector, recorder, integrator, etc.

Various substances of known polarity are injected into the chromatographic column. These substances are representative of the various organic functional groups, such as primary alcohol, tertiary alcohol, amines, halogenated products, aromatic hydrocarbons, aliphatic and cyclic ketones, thiophenes, a mixture of normal paraffins, etc. For each substance, its retention time in the column is determined. An inert substance which does not interact with the stationary phase, such as air or methane is injected simultaneously with each test substance. The corrected retention time for a substance is the time elapsed between the detection of the inert substance and the detection of the known substance.

From the retention time can be calculated the retention index as described by KOVATS and ETTRE supra, the calculation being shown hereafter.

A second column is then prepared, using the same technique but with a fully non-polar stationary phase, such as squalane or apolane, or another non-polar hydrocarbon.

Into this second column are injected the same known substances which were injected into the column containing crude oil, in the same chromatographic conditions of operation. The corrected retention times and retention indices are determined for each substance.

Thus, each known substance has two retention indices, one for each column into which it was injected.

For each known substance a third quantity is then calculated, which is a function of the two retention index values and is usually the difference between the two retention indices. A mathematical function of all third quantities for the injected substances should represent the difference between the interactions undergone in a fully non-polar substance (squalane, apolane or similar) considered of zero polarity and those undergone in the polar substance which is to be classified (petroleum or petroleum product). This number represents the relative polarity of the crude oil or its product. The mathematical function of the third quantities is preferably the sum of the differences in retention indices.

Both the retention times and the retention indices are ways of quantifying the interactions between the stationary phase and the substance. Other ways of quantifying interaction may be used.

The following three examples illustrate and show the operational details of the process of the present invention:

EXAMPLE 1

A volume of nearly 500 ml of crude oil A, from Southeast Brazil, was distilled, providing the 260° C.+ cut. A solution of 0.2 g of this heavy fraction was prepared in 30 ml of benzene, then added to 20 g of Vollaspher A2 support, 80/100 mesh. The solvent was evaporated under vacuum, at 60° C., in a rotating evaporator, until fully dry granules were obtained. Such granules of stationary phase and support were used to fill a metallic tube, 39.5 in (1 meter) long with ⅛" (0.32 cm) ID. This tube constitutes the column, which was placed inside a chromatographic apparatus and conditioned at 100° C. during 12 hours, under a nitrogen flow of 10 ml/min.

After this period the apparatus was prepared to operate at temperature of 100° C. in the column, 250° C. in the injector and in the detector, and under a gas dragging flow of 10 ml/min.

The following substances were injected: 1-butanol, 2-pentanone, benzene, pyridine, triethylamine, 2-nitropropane, 2-methyl-2-pentanol, dioxane, iodobutane, thiophene and a mixture of normal paraffins including n-pentane to n-nonane. Each substance was injected together with methane, which made it possible to determine its corrected retention time.

The retention index is given by $$I = \frac{100[\log x_i - \log x_{(n-C_z)}]}{\log x_{(n-C_{z+1})} - \log X_{(n-C_z)}} + 100 Z$$

Here, $x_i$ is the corrected retention time for substance i which has Z carbon atoms; $x_{(n-C_z)}$ is the corrected retention time for the normal paraffin with Z carbon atoms, eluted before the substance i; $x_{(n-C_{z+1})}$ is the corrected retention time for the normal paraffin with Z+1 carbon atoms, eluted before the substance i.

For each substance i injected the retention index in the column was calculated.

The operation was repeated with crude oils B and C, also from Southeast Brazil.

The operation was then repeated using squalane as the stationary phase, in the proportion of 0.2 g of squalane to 1.0 g of Vollaspher A2, 80/100 mesh, but using normal hexane as solvent. The remaining procedure was identical to that adopted for crude oils A,B and C.

Table I lists the results obtained, the differences between the retention indices of each crude oil and those of squalane, and the sum of these differences for each crude oil, that is the relative polarity.

From the results achieved it can be seen that crude oil A is the most polar (558.1), followed by crude oil B (449.3) and crude oil C (402.9), in this order. In addition, it may be affirmed that crude oil A is almost 40% more polar that crude oil C. Larger difficulties relating to water/oil separation in production operations may be then, anticipated for the former.

EXAMPLE 2

A comparison of the polarities of two fractions of asphaltenes, obtained from two Northeastern crude oils, is desired. An amount of 0.2 g of each fraction was weighed and dissolved in 50 ml of benzene. Each solution was poured over 2.0 of Chemosorb W, 60/80 mesh. Thereafter it was processed as in Example 1, and the results obtained are listed in Table II.

From these results it was found that the asphaltenes studied are very similar as far as their polarity is concerned, differing in less than 10% from each other. Their properties are very similar and their applications can be similar.

EXAMPLE 3

To determine the polarity of three vacuum residua respectively from Iran, onshore Sergipe and light Arabian crudes, three solutions were prepared hot from 0.2 g of each residuum and portions of 50 ml of toluene. Each solution was added to 2.0 g of Vollaspher A2 80/100 mesh and evaporated as described in Example 1. The remaining procedure was as in Example 1, and the results obtained are set out in Table III.

It was thus found that the most polar vacuum residuum is that of the Iran crude, followed by the onshore Sergipe and by the light Arabian. Therefore, the properties of the vacuum residuum from the Iran crude make it more easily emulsionable for burning and transportation.

TABLE I

| POLARITY RESULTS OBTAINED FOR CRUDE OILS A, B AND C FROM SOUTHEAST BRAZIL | | | | | | | | | | | |
|---|---|---|---|---|---|---|---|---|---|---|---|
| SUBSTANCES | CRUDE OIL A | | CRUDE OIL B | | CRUDE OIL C | | SQUALANE | | ΔI | | |
| INJECTED$_{(i)}$ | $x_i$ | $I_i$ | $x_i$ | $I_i$ | $x_i$ | $I_i$ | $x_i$ | $I_i$ | A | B | C |
| butanol-1 | 0.54 | 673.4 | 0.58 | 657.4 | 0.43 | 650.8 | 0.70 | 596.2 | 77.2 | 61.2 | 54.6 |
| 2-pentanone | 0.60 | 687.4 | 0.67 | 675.8 | 0.51 | 672.8 | 0.88 | 626.9 | 60.5 | 48.9 | 45.9 |
| triethylamine | 0.66 | 700.0 | 0.77 | 693.5 | 0.59 | 691.6 | 1.31 | 680.1 | 19.9 | 13.4 | 11.5 |
| benzene | 0.63 | 693.8 | 0.74 | 688.5 | 0.53 | 677.7 | 1.04 | 649.2 | 44.6 | 39.3 | 28.5 |
| thiophene | 0.72 | 711.5 | 0.83 | 703.2 | 0.58 | 689.3 | 1.08 | 654.2 | 57.3 | 49.0 | 35.1 |
| dioxane | 0.72 | 711.5 | 0.84 | 704.7 | 0.61 | 695.8 | 1.10 | 656.7 | 54.8 | 48.0 | 39.1 |
| 2-nitropropane | 0.91 | 739.4 | 0.98 | 724.7 | 0.70 | 714.0 | 1.07 | 653.0 | 86.4 | 71.7 | 61.0 |
| 2-methyl-2-pentanol | 0.89 | 742.3 | 1.01 | 728.7 | 0.79 | 730.0 | 1.46 | 694.6 | 47.7 | 34.1 | 35.4 |
| pyridine | 1.37 | 796.2 | 1.49 | 779.1 | 1.03 | 765.1 | 1.53 | 700.8 | 95.5 | 78.4 | 64.4 |
| iodobutane | 2.31 | 866.6 | 2.70 | 857.5 | 1.95 | 850.2 | 3.66 | 814.4 | 52.2 | 43.1 | 35.8 |
| n-pentane | 0.13 | 500.0 | 0.16 | 500.0 | 0.13 | 500.0 | 0.35 | 500.0 | 0 | 0 | 0 |
| n-hexane | 0.31 | 600.0 | 0.37 | 600.0 | 0.29 | 600.0 | 0.72 | 600.0 | 0 | 0 | 0 |
| n-heptane | 0.66 | 700.0 | 0.81 | 700.0 | 0.63 | 700.0 | 1.52 | 700.0 | 0 | 0 | 0 |
| n-octane | 1.41 | 800.0 | 1.75 | 800.0 | 1.34 | 800.0 | 3.31 | 800.0 | 0 | 0 | 0 |
| n-nonane | 2.96 | 900.0 | 3.72 | 900.0 | 2.83 | 900.0 | 6.64 | 900.0 | 0 | 0 | 0 |
| ΣΔI | — | — | — | — | — | — | — | — | 596.1 | 487.1 | 411.3 | where:
$x_i$ - retention time corrected for substance i.
I - retention index of each substance i.
ΔI - difference of the retention index of substance i in crude oil and squalane.
ΣΔI - sum of differences of retention indices - represents the relative polarity of each crude oil.

TABLE II

| POLARITY RESULTS OBTAINED FOR ASPHALTENES FROM NORTHEASTERN CRUDE OILS | | | | | | | | |
|---|---|---|---|---|---|---|---|---|
| SUBSTANCES | ASPHALTENE A | | ASPHALTENE B | | SQUALANE | | ΔI | |
| INJECTED$_{(i)}$ | $x_i$ | $I_i$ | $x_i$ | $I_i$ | $x_i$ | $I_i$ | ASPHALTENE A | ASPHALTENE B |
| benzene | 0.10 | 732.2 | 0.09 | 717.0 | 1.04 | 649.2 | 83.0 | 67.8 |
| 2-pentanone | 0.11 | 746.0 | 0.11 | 745.9 | 0.88 | 626.9 | 119.1 | 119.0 |
| thiophene | 0.12 | 758.5 | 0.11 | 745.9 | 1.08 | 654.3 | 104.2 | 91.6 |
| dioxane | 0.13 | 770.0 | 0.12 | 758.5 | 1.10 | 656.7 | 113.3 | 101.8 |
| butanol-1 | 0.15 | 791.0 | 0.14 | 780.7 | 0.70 | 596.2 | 194.8 | 184.5 |
| 2-methyl-2-pentanol | 0.17 | 808.4 | 0.16 | 800.0 | 1.46 | 694.6 | 113.8 | 105.4 |
| 2-nitropropane | 0.19 | 823.7 | 0.18 | 816.3 | 1.07 | 653.0 | 170.7 | 163.3 |
| iodobutane | 0.33 | 900.0 | 0.31 | 891.4 | 3.66 | 814.4 | 85.6 | 77.0 |
| n-heptane | 0.08 | 700.0 | 0.08 | 700.0 | 1.52 | 700.0 | 0 | 0 |
| n-octane | 0.16 | 800.0 | 0.16 | 800.0 | 3.31 | 800.0 | 0 | 0 |
| n-nonane | 0.33 | 900.0 | 0.33 | 900.0 | 6.64 | 900.0 | 0 | 0 |

TABLE II-continued
POLARITY RESULTS OBTAINED FOR ASPHALTENES FROM NORTHEASTERN CRUDE OILS

| SUBSTANCES | ASPHALTENE A | | ASPHALTENE B | | SQUALANE | | ΔI | |
|---|---|---|---|---|---|---|---|---|
| INJECTED$_{(i)}$ | $x_i$ | $I_i$ | $x_i$ | $I_i$ | $x_i$ | $I_i$ | ASPHALTENE A | ASPHALTENE B |
| ΣΔI | — | — | — | — | — | — | 984.5 | 910.4 |

REMARKS: Same symbols as in Table I.

TABLE III
POLARITY RESULTS OBTAINED FOR VACUUM RESIDUES FROM VARIOUS SOURCES

| | VACUUM RESIDUE FROM IRAN CRUDE OIL | | VACUUM RESIDUE FROM ONSHORE SERGIPE CRUDE OIL | | VACUUM RESIDUE FROM LIGHT ARABIAN CRUDE OIL | | SQUALANE | | ΔI VACUUM RESIDUE FROM IRAN CRUDE OIL | ΔI VACUUM RESIDUE FROM ONSHORE SERGIPE CRUDE OIL | ΔI VACUUM RESIDUE FROM LIGHT ARABIAN CRUDE OIL |
|---|---|---|---|---|---|---|---|---|---|---|---|
| SUBSTANCES INJECTED | $x_i$ | $I_i$ | $x_i$ | $I_i$ | $x_i$ | $I_i$ | $x_i$ | $I_i$ | | | |
| 2-pentanone | 0.80 | 714.1 | 0.73 | 713.5 | 0.70 | 698.3 | 0.88 | 626.9 | 87.2 | 86.6 | 71.4 |
| butanol-1 | 0.84 | 720.6 | 0.73 | 713.5 | 0.68 | 694.8 | 0.70 | 596.2 | 124.4 | 117.3 | 98.6 |
| benzene | 0.85 | 722.2 | 0.75 | 717.2 | 0.78 | 712.3 | 1.04 | 649.2 | 73.0 | 68.0 | 63.1 |
| thiophene | 0.99 | 742.6 | 0.87 | 737.1 | 0.89 | 729.7 | 1.08 | 654.3 | 88.3 | 82.8 | 75.4 |
| dioxane | 1.02 | 746.6 | 0.94 | 747.5 | 0.89 | 729.7 | 1.10 | 656.7 | 89.9 | 90.8 | 73.0 |
| 2-methyl-2-pentanol | 1.26 | 774.9 | 0.73 | 713.5 | 1.06 | 752.7 | 1.46 | 694.6 | 80.3 | 18.9 | 58.1 |
| nitropropane | 1.40 | 789.0 | 1.16 | 775.7 | 1.19 | 767.9 | 1.07 | 653.0 | 136.0 | 122.7 | 114.9 |
| iodobutane | 3.01 | 894.2 | 2.60 | 886.8 | 2.76 | 880.8 | 3.66 | 814.4 | 79.8 | 72.4 | 66.4 |
| n-hexane | 1.33 | 600.0 | 0.30 | 600.0 | 0.31 | 600.0 | 0.72 | 600.0 | 0 | 0 | 0 |
| n-heptane | 0.72 | 700.0 | 0.66 | 700.0 | 0.71 | 700.0 | 1.52 | 700.0 | 0 | 0 | 0 |
| n-octane | 1.52 | 800.0 | 1.39 | 800.0 | 1.52 | 800.0 | 3.31 | 800.0 | 0 | 0 | 0 |
| n-nonane | 3.14 | 900.0 | 2.86 | 900.0 | 3.18 | 900.0 | 6.64 | 900.0 | 0 | 0 | 0 |
| ΣΔI | — | — | — | — | — | — | — | — | 758.9 | 659.5 | 620.9 |

REMARKS: Same symbols as in Table I.

I claim:

1. A process for determining the relative polarity of a crude oil or fraction thereof comprising:

(a) contacting a known test substance with a stationary phase of the crude oil or fraction in a gas chromatography column, and measuring the interaction between the test substance and the oil;

(b) contacting the known test substance used in (a) with a stationary phase of a non-polar second substance in a gas chromatography column and measuring the interaction between the test substance and the non-polar second substance;

(c) determining the polarity of the crude oil relative to the non-polar second substance from the measurements obtained in (a) and (b).

2. A process according to claim 1 in which the known substance is selected from the group consisting of a hydrocarbon, an alcohol, an amine, a ketone, a thiophene, a halogen-substituted hydrocarbon, a halogen-substituted alcohol, a halogen-substituted amine, a halogen-substituted ketone, a halogen-substituted thiophene, a nitro-substituted hydrocarbon, a nitro-substituted alcohol, a nitro-substituted amine, a nitro-substituted ketone, and a nitro-substituted thiophene.

3. A process according to claim 1 or 2 in which the crude oil does not contain components whose boiling points are below 200° C.

4. A process according to any one of claims 1 or 2, in which the interactions measured in steps (a) and (b) are the retention times of the test substances in the columns.

5. A process according to claim 1, wherein the non-polar second substance is a non-polar hydrocarbon.

6. A process according to claim 5, wherein the non-polar hydrocarbon is selected from the group consisting of squalane and apolane.

7. A process according to claim 3 in which the interactions measured in steps (a) and (b) are the retention times of the test substances in the column.

* * * * *